(12) United States Patent
Quy

(10) Patent No.: US 9,943,723 B2
(45) Date of Patent: *Apr. 17, 2018

(54) METHOD AND APPARATUS FOR EXERCISE MONITORING COMBINING EXERCISE MONITORING AND VISUAL DATA WITH WIRELESS WEARABLE DEVICES

(71) Applicant: KONINKLIJKE PHILIPS N.V., Eindhoven (NL)

(72) Inventor: Roger J. Quy, Kentfield, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,711

(22) Filed: Feb. 26, 2016

(65) Prior Publication Data
US 2016/0175652 A1    Jun. 23, 2016

Related U.S. Application Data

(63) Continuation of application No. 14/220,682, filed on Mar. 20, 2014, now Pat. No. 9,272,183, which is a
(Continued)

(51) Int. Cl.
*A63B 24/00* (2006.01)
*A61B 5/00* (2006.01)
(Continued)

(52) U.S. Cl.
CPC ........ *A63B 24/0062* (2013.01); *A61B 5/0013* (2013.01); *A61B 5/0022* (2013.01);
(Continued)

(58) Field of Classification Search
CPC . A63B 24/0062; A61B 5/0013; A61B 5/0022; A61B 5/0077; A61B 5/1112;
(Continued)

(56) References Cited

U.S. PATENT DOCUMENTS 4,282,883 A    8/1981    Yerushalmy
5,012,814 A    5/1991    Mills et al.
(Continued)

FOREIGN PATENT DOCUMENTS

GB    2326237    12/1998
JP    9224917    9/1997
(Continued)

OTHER PUBLICATIONS

U.S. Appl. No. 601264,739, filed Jan. 2001, Posa et al.
(Continued)

*Primary Examiner* — Catherine Voorhees

(57) ABSTRACT

Embodiments of the invention provide a method and apparatus for a wireless exercise monitoring system for interactively monitoring an aspect of exercise, sports, or fitness utilizing a wearable device, such as a watch, eyewear, or smart apparel. The device is equipped with, or connected to, a digital camera. Sensors integrated with, or wirelessly connected to, the wearable internet device record physiological data during exercise and data measuring the amount of exercise performed. The data and visual images from the camera are transmitted to one or more internet servers, and may be shared with other mobile internet devices.

11 Claims, 8 Drawing Sheets

Related U.S. Application Data continuation-in-part of application No. 12/692,080, filed on Jan. 22, 2010, now Pat. No. 8,712,510, which is a continuation-in-part of application No. 11/649,355, filed on Jan. 3, 2007, now abandoned, which is a continuation of application No. 11/156,177, filed on Jun. 17, 2005, now Pat. No. 7,156,809, which is a continuation-in-part of application No. 10/773,501, filed on Feb. 6, 2004, now Pat. No. 6,976,958.

(51) Int. Cl.

| | | |
|---|---|---|
| *G06F 19/00* | (2011.01) | |
| *G08B 21/02* | (2006.01) | |
| *G08B 21/04* | (2006.01) | |
| *H04N 1/00* | (2006.01) | |
| *H04N 7/18* | (2006.01) | |
| *H04N 21/414* | (2011.01) | |
| *H04N 21/422* | (2011.01) | |
| *H04N 21/4223* | (2011.01) | |
| *H04N 21/442* | (2011.01) | |
| *H04N 21/4782* | (2011.01) | |
| *A61B 5/11* | (2006.01) | |
| *A63B 22/00* | (2006.01) | |
| *A63B 22/02* | (2006.01) | |
| *A63B 22/06* | (2006.01) | |
| *H04N 5/232* | (2006.01) | |
| *A61B 5/021* | (2006.01) | |
| *A61B 5/024* | (2006.01) | |
| *A61B 5/0432* | (2006.01) | |
| *A61B 5/145* | (2006.01) | |
| *H04W 24/00* | (2009.01) | |
| *H04W 88/02* | (2009.01) | |

(52) U.S. Cl.
CPC .......... *A61B 5/0077* (2013.01); *A61B 5/1112* (2013.01); *A61B 5/6801* (2013.01); *A61B 5/6826* (2013.01); *A61B 5/6838* (2013.01); *A61B 5/743* (2013.01); *A63B 22/0076* (2013.01); *A63B 22/02* (2013.01); *A63B 22/0605* (2013.01); *A63B 22/0664* (2013.01); *A63B 24/0021* (2013.01); *G06F 19/3418* (2013.01); *G06F 19/3481* (2013.01); *G08B 21/02* (2013.01); *G08B 21/0211* (2013.01); *G08B 21/04* (2013.01); *H04N 1/00127* (2013.01); *H04N 1/00244* (2013.01); *H04N 5/23293* (2013.01); *H04N 7/185* (2013.01); *H04N 21/41407* (2013.01); *H04N 21/4223* (2013.01); *H04N 21/42201* (2013.01); *H04N 21/44213* (2013.01); *H04N 21/4782* (2013.01); *A61B 5/0008* (2013.01); *A61B 5/021* (2013.01); *A61B 5/02438* (2013.01); *A61B 5/04325* (2013.01); *A61B 5/14532* (2013.01); *A61B 2562/0219* (2013.01); *G06F 19/322* (2013.01); *G06F 19/3456* (2013.01); *G06F 19/3475* (2013.01); *H04N 1/00307* (2013.01); *H04N 2201/0084* (2013.01); *H04W 24/00* (2013.01); *H04W 88/02* (2013.01); *Y10S 128/903* (2013.01); *Y10S 128/904* (2013.01)

(58) Field of Classification Search
CPC ... A61B 5/6801; A61B 5/6826; A61B 5/6838; A61B 5/743; A61B 22/02; A61B 22/0076
See application file for complete search history.

(56) References Cited

U.S. PATENT DOCUMENTS

| | | |
|---|---|---|
| 5,307,263 A | 4/1994 | Brown |
| 5,357,427 A | 10/1994 | Langen et al. |
| 5,410,471 A | 4/1995 | Alyfuku et al. |
| 5,434,611 A | 7/1995 | Tamura |
| 5,441,047 A | 8/1995 | David et al. |
| 5,474,090 A | 12/1995 | Begun et al. |
| 5,544,649 A | 8/1996 | David et al. |
| 5,544,661 A | 8/1996 | Davis et al. |
| 5,549,117 A | 8/1996 | Tacklind et al. |
| 5,553,609 A | 9/1996 | Chen |
| 5,576,952 A | 11/1996 | Strutman et al. |
| 5,601,435 A | 2/1997 | Quy |
| 5,626,144 A | 5/1997 | Tacklind et al. |
| 5,678,562 A | 10/1997 | Sellers |
| 5,701,904 A | 12/1997 | Simmons et al. |
| 5,704,366 A | 1/1998 | Tacklind et al. |
| 5,724,025 A | 3/1998 | Tavori |
| 5,732,709 A | 3/1998 | Tacklind et al. |
| 5,735,285 A | 4/1998 | Albert et al. |
| 5,752,917 A | 5/1998 | Fuchs |
| 5,772,586 A | 6/1998 | Heinonen et al. |
| 5,791,342 A | 8/1998 | Woodard |
| 5,929,782 A | 7/1999 | Stark et al. |
| 5,931,791 A | 8/1999 | Saltzstein et al. |
| 5,933,136 A | 8/1999 | Brown |
| 5,935,060 A | 8/1999 | Iliff |
| 5,941,829 A | 8/1999 | Saltzstein et al. |
| 5,951,300 A | 9/1999 | Brown |
| 5,959,533 A | 9/1999 | Layson et al. |
| 5,964,701 A | 10/1999 | Asada et al. |
| 5,967,975 A | 10/1999 | Ridgeway |
| 5,987,352 A | 11/1999 | Klein et al. |
| 5,987,519 A | 11/1999 | Peifer et al. |
| 5,997,476 A | 12/1999 | Brown |
| 6,013,007 A | 1/2000 | Root et al. |
| 6,022,315 A | 2/2000 | Iliff |
| 6,024,699 A | 2/2000 | Surwit et al. |
| 6,050,940 A | 4/2000 | Braun et al. |
| 6,055,506 A | 4/2000 | Frasca, Jr. |
| 6,057,758 A | 5/2000 | Dempsey et al. |
| 6,059,692 A | 5/2000 | Hickman et al. |
| 6,083,156 A | 7/2000 | Leseicki |
| 6,093,146 A | 7/2000 | Filangeri |
| 6,101,478 A | 8/2000 | Brown |
| 6,144,837 A | 11/2000 | Quy |
| 6,160,478 A | 12/2000 | Jacobsen et al. |
| 6,168,563 B1 | 1/2001 | Brown |
| 6,190,324 B1 | 2/2001 | Kieval et al. |
| 6,266,645 B1 | 7/2001 | Simpson et al. |
| 6,309,342 B1 | 10/2001 | Blazey et al. |
| 6,319,199 B1 | 11/2001 | Sheehan et al. |
| 6,336,900 B1 | 1/2002 | Aleckson et al. |
| 6,353,839 B1 | 3/2002 | King et al. |
| 6,375,614 B1 | 4/2002 | Braun et al. |
| 6,386,882 B1 | 5/2002 | Linberg |
| 6,416,471 B1 | 7/2002 | Kumar et al. |
| 6,418,346 B1 | 7/2002 | Nelson et al. |
| 6,440,068 B1 | 8/2002 | Brown et al. |
| 6,450,955 B1 | 9/2002 | Brown et al. |
| 6,458,080 B1 | 10/2002 | Brown et al. |
| 6,478,736 B1 | 11/2002 | Mault |
| 6,524,189 B1 | 2/2003 | Rautila |
| 6,529,771 B1 | 3/2003 | Kieval et al. |
| 6,602,191 B2 | 8/2003 | Quy |
| 6,605,038 B1 | 8/2003 | Teller et al. |
| 6,610,012 B2 | 8/2003 | Mault |
| 6,702,719 B1 | 3/2004 | Brown et al. |
| 6,736,759 B1 | 5/2004 | Stubbs et al. |
| 6,790,178 B1 | 9/2004 | Mault |
| 6,816,603 B2 | 11/2004 | David et al. |
| 6,856,832 B1 | 2/2005 | Matsumura et al. |
| 6,936,007 B2 | 8/2005 | Quy |
| 6,976,958 B2 | 12/2005 | Quy |
| 7,156,809 B2 | 1/2007 | Quy |
| 7,602,301 B1 | 10/2009 | Stirling et al. |

(56) References Cited

U.S. PATENT DOCUMENTS

| | | | |
|---|---|---|---|
| 7,739,130 B2 | 6/2010 | Surwit et al. | |
| 8,712,510 B2* | 4/2014 | Quy | A61B 5/6826 600/508 |
| 9,272,183 B2* | 3/2016 | Quy | A61B 5/1112 |
| 2001/0005830 A1 | 6/2001 | Kuroyanagi | |
| 2001/0047125 A1* | 11/2001 | Quy | A61B 5/7465 600/300 |
| 2002/0016719 A1* | 2/2002 | Nemeth | G06Q 50/22 705/2 |
| 2002/0019584 A1 | 2/2002 | Schultze et al. | |
| 2002/0026223 A1 | 2/2002 | Riff et al. | |
| 2002/0045519 A1 | 4/2002 | Watterson et al. | |
| 2002/0072785 A1 | 6/2002 | Nelson et al. | |
| 2002/0082480 A1 | 6/2002 | Riff et al. | |
| 2002/0109600 A1* | 8/2002 | Mault | A61B 5/1112 340/573.1 |
| 2002/0120310 A1 | 8/2002 | Linden et al. | |
| 2002/0160883 A1* | 10/2002 | Dugan | A63B 24/00 482/8 |
| 2003/0004554 A1 | 1/2003 | Riff et al. | |
| 2003/0036683 A1 | 2/2003 | Kehr et al. | |
| 2003/0065257 A1 | 4/2003 | Mault et al. | |
| 2003/0072424 A1 | 4/2003 | Evans et al. | |
| 2003/0134714 A1 | 7/2003 | Oishi et al. | |
| 2003/0139785 A1 | 7/2003 | Riff et al. | |
| 2003/0204413 A1 | 10/2003 | Riff | |
| 2004/0030226 A1 | 2/2004 | Quy | |
| 2004/0162466 A1 | 8/2004 | Quy | |
| 2005/0038326 A1 | 2/2005 | Mathur | |
| 2005/0080322 A1 | 4/2005 | Korman | |
| 2005/0228245 A1 | 10/2005 | Quy | |
| 2007/0033154 A1 | 2/2007 | Trainum et al. | |
| 2009/0093341 A1* | 4/2009 | James | A63B 24/0062 482/1 |
| 2010/0120585 A1 | 5/2010 | Quy | |
| 2010/0298656 A1 | 11/2010 | McCombie et al. | |
| 2013/0019694 A1 | 1/2013 | Molyneux et al. | |
| 2013/0090565 A1 | 4/2013 | Quy | |

FOREIGN PATENT DOCUMENTS

| | | |
|---|---|---|
| JP | 11047101 | 2/1999 |
| JP | 11122369 | 4/1999 |
| JP | 11259783 | 9/1999 |
| JP | 2002/344660 | 11/2002 |
| KR | 10-0474926 B1 | 3/2005 |
| KR | 10-2008-0028577 A | 4/2008 |
| KR | 10-2008-0098457 A | 11/2008 |
| WO | 95/32480 | 11/1995 |
| WO | 97/28736 | 8/1997 |
| WO | 97/28739 | 8/1997 |
| WO | 98/24358 | 6/1998 |
| WO | 98/38909 | 9/1998 |
| WO | 99/04687 | 2/1999 |
| WO | 99/41682 | 8/1999 |
| WO | 99/44494 | 9/1999 |
| WO | 99/46718 | 9/1999 |
| WO | 00/36900 | 6/2000 |
| WO | 00/40145 | 7/2000 |
| WO | 00/54205 | 9/2000 |
| WO | 00/54206 | 9/2000 |
| WO | 00/62662 | 10/2000 |
| WO | 01/24038 | 4/2001 |

OTHER PUBLICATIONS

"Bluetooth Technical Background" press release from May 26, 1998. Found at http://web.archive.org/web/19990427070 1411www.bluetooth.comldefault.asp.

Jyrki Oraskari; "Bluetooth versus WLAN IEEE 802. llx"; Helsinki University of Technology (Department of Computer Science and Engineering) Nov. 2000.

Jack Smith; Your Personal Health Buddy; ABCNews.com; http:/abcnews.go.comisections/tech/CuttingEdge/cuttingedge990225.html; 3 pages (Nov. 24, 2000).

The Health Hero Communications Platform; The Health Hero Network Online Services; http:/www.hhn.comlproductslindex.html; 2 pages (Nov. 24, 2000).

Painless Blood-Glucose Monitoring; Kumertrix Technology Overview; http:/www.kumertrix.comltechnology.html; 2 pages; Nov. 24, 2000.

Technology & Clinical Results—Simple Solutions Through Technology—Progression of Glucose Monitoring Technology; Amira; http:/amira.comltechlic_tech.htm; 2 pages; Nov. 24, 2000.

Wired for Wellness; LifeChart.com; http:/www.lifechart.com; 2 pages; Nov. 24, 2000.

About data Critical Corporation; Yahoo-data Critical to Provide Mallincrodt with Wireless Connectivity for Ventilators; http:/biz.yahoo.comipmews/OO 102/mo_mallinc.html; 1 page; Nov. 24, 2000.

Bluetooth wireless technology—bridging the gap between computing and communication; Bluetooth Technology; http://www.intell.commobile/bluetooth/; 2 pages; Nov. 28, 2000.

Bluetooth resource center: What is Bluetooth?; palowireless.com; http:/www.palowireless.comlinfotooth/watis.asp; 3 pages; Nov. 28, 2000.

Bluetooth Tutorial; palowireless.com—Bluetooth resource center; http://www.palowireless.comlinfortooth/tutorial.asp; 4 pages; Nov. 28, 2000.

Nick Hunt; Bluetooth Venus 802.11; TDK Systems; http://www.cellular.com.zalbluetooth_versus_802.htm; 4 pages; Nov. 28, 2000.

Bluetooth vs. Airport (802.11 Network); palowireless.com Bluetooth resource center; http://www.palowireless.comlinfotooth/knowbase/ofthenetworksl15asp; 3 pages; Nov. 28, 2000.

Personal Digital Assistants; A2 Anytime/anywhere-a Weekly on Wireless Infrastructure and Data Services; Thomas Weisel Partners (Merchant Banking); 5 pages; Nov. 29, 2000.

Ashlee Vance; Ericsson and Intel Make Bluetooth Pact; InfoWorld.com; http://www.infoworld.comlarticles/hn/xml/OO/12/047/001204hnericitel.xml?T..'!printarticle.htm; 1 page; Dec. 4, 2000.

Personal Portable Office; Nokia 9000lldigital; http://www.nokiausa.coml900011; 4 pages; Dec. 7, 2000.

Pul-Wing Tam; Handspring Homes; Article from the Wall Street Journal; Section B; Nov. 2000.

Author unknown; Articles on Phones and New Technologies; Article from the Wall Street Journal; Nov. 2000.

David Pringle; Sagen to Launch hand-held computer that doubles as top-end mobile phone; Article from the Wall Street Journal; Nov. 2000.

Svensson, Peter; "Cisco Launches WiFi Phone" Article from Australian IT; Apr. 29, 2003.

"Breakthrough Devices Shown at ADA" published in Diabetes News for Jul. 1, 2001 at http://www.diabetesnet.cominews/news070 101.php.

"Applications of MedStar" published on Apr. 27, 2003 by Cybernet Medical, 16 pages.

"Medtronic CareLink Network, How it Works" published at http://www.medtronic.comlcarelink/features.html. (Retrieved Jun. 2004).

"FDA Approves Medtronic CareLinkTM Monitor and Software, Opening a New Chapter in Patient Management Using Internet Technology", Medtronic News Release dated Jan. 2, 2002.

"IMetrikus Mobile Solutions" brochure by IMetrikus, Inc. (Retrieved Jun. 2004).

"Instromedix—Products" published at www.instromedix.com/pages/products/products.asp 7 pages. (Retrieved Jun. 2004).

EFI Framework Draft Version 0.8 (Jun. 3, 2000): External functionality Interface Framework; pp. 1-35.

Internet Press Release: New York Business Wire (Sep. 25, 2000); MedSearch Technologies, Inc. Develops a Revolutionary HomeCare Wireless Technology Utilizing PDAs—Personal Organizers—as Patient Monitors.

"Cell Phone Cameras Put Doctors in the Picture", Feb. 21, 2005, 1 page, http://news.healingwell.comlindex.php?p-newsl&id-524118.

Yan Xiao, PhD, et al. "Design and Evaluation of a Real-Time Mobile Telemedicine System for Ambulance Transport", Proceed-

(56) References Cited

OTHER PUBLICATIONS ings of the 1998 American Medical Informatics Association Annual Fall Symposium, 1998, pp. 1102-1103.

Yan Xiao, PhD et al. "Design and Evaluation of a Real-Time Mobile Telemedicine System for Ambulance Transport", The Journal of High Speed Networks, 2000, vol. 9(1), pp. 47-58.

Ky Kong et al., "Web-Based Monitoring of Real-Time ECG Data", Computers in Cardiology, 2000, vol. 27, pp. 189-192.

Juha Parkka et al. "A Wireless Wellness Monitor for Personal Weight Management", Proc. 2000 IEEE EMBS Int'L Conf. on Info Tech. Applications in Biomedicine, 2000, pp. 83-88.

Joseph Finkelstein et al. "Web-based Monitoring of Asthma Severity: A New Approach to Ambulatory management", Proc. 1998 IEEE Int'l Conf. on Info Tech. Applications in Biomedicine, 1998, pp. 139-143.

Gary D. Havey et al. "A Wearable Polysomnograph With an RF Link to a Personal Computer, Recorder, or the Internet", Proceedings of the nnd Annual EMBS International Conference, Jul. 23-28, 2000, p. 1264.

Emil Jovanov et al. Stress Monitoring Using a Distributed Wireless Intelligent Sensor System:, IEEE Engineering in Medicine and Biology Magazine, May/Jun. 2003, pp. 49-55.

SP Nelwan et al. "Ubiquitous Mobile Access to Real-Time Patient Monitoring Data", Computers in Cardiology, 2002, vol. 29, pp. 557-560.

Brent Priddy et al., "Wireless Distributed Data Acquisition System", 2002 IEEE, pp. 463-466.

Emil Jovanov et al. "Prolonged Telemetric Monitoring of Heart Rate Variability Using Wireless Intelligent Sensors and a Mobile Gateway", Proceedings of the Second Joint EMBS/BMES Conference, Oct. 23-26, 202, pp. 1875-1876.

"Bluetooth Technical Background" Press releast from May 26.Yan Xiao et al., Design and Evaluation of a Real-Time Mobile Telemedicine System for Ambulance Transport, Proceedings of the AMIA Symposium, 1998, p. 1102.

International Search Report and Written Opinion dated Jun. 19, 2015, issued in connection with corresponding International Application No. PCT/US15/20919 (10 pages total).

Patent Examination Report dated Sep. 30, 2015 in connection with corresponding Australian Patent Application No. 2011207170 (3 pages total).

* cited by examiner ative communication of medical or health information between a subject or patient and a reviewer or provider of that information. However, in general, previous systems have limited the user to the general location in which the device was located. For example, in U.S. Pat. No. 5,441,047, images and data were transmitted by standard telephone lines or wireless telemetry systems.

METHOD AND APPARATUS FOR EXERCISE MONITORING COMBINING EXERCISE MONITORING AND VISUAL DATA WITH WIRELESS WEARABLE DEVICES

CROSS-REFERENCE TO RELATED APPLICATIONS

This application is a continuation of U.S. patent application Ser. No. 14/220,682, filed Mar. 20, 2014, entitled "Method and Apparatus For Exercise Monitoring Combining Exercise Monitoring and Visual Data With Wireless Wearable Devices," now U.S. Pat. No. 9,272,183, which is a continuation-in-part of U.S. patent application Ser. No. 12/692,080, filed Jan. 22, 2010, entitled "Method and Apparatus For Exercise Monitoring Combining Exercise Monitoring and Visual Data With Wireless Internet Connectivity," now U.S. Pat. No. 8,712,510, which is a continuation-in-part of U.S. patent application Ser. No. 11/649,355, filed Jan. 3, 2007, entitled "Method and Apparatus For Health and Disease Management Combining Patient Data Monitoring With Wireless Internet Connectivity," now abandoned, which is a continuation of U.S. patent application Ser. No. 11/156,177, filed Jun. 17, 2005, entitled "Method and Apparatus For Health and Disease Management Combining Patient Data Monitoring With Wireless Internet Connectivity," now U.S. Pat. No. 7,156,809, which is a continuation-in-part of U.S. patent application Ser. No. 10/773,501, filed Feb. 6, 2004, now U.S. Pat. No. 6,976,958, the entirety of each prior application being incorporated by reference herein.

REFERENCE TO GOVERNMENTAL SUPPORT (none)

REFERENCE TO MICROFICHE APPENDIX (none)

FIELD OF THE INVENTION

The present invention relates to monitoring of living subjects, such as during exercise, and more particularly to exercise monitoring of persons where measured or input exercise data is communicated by a mobile communications device to and from the internet.

BACKGROUND OF THE INVENTION

Several attempts have been made in the past to achieve efficient interactive communication of medical or health information between a subject or patient and a reviewer or provider of that information. However, in general, previous systems have limited the user to the general location in which the device was located. For example, in U.S. Pat. No. 5,441,047, images and data were transmitted by standard telephone lines or wireless telemetry systems.

Even where devices are portable, as in the case of a laptop computer with a modem, an ordinary POTS phone line must be found and used. Where the user's computer employs a broadband connection, such as DSL or satellite, the choices of location are even more limited.

Attempts have been made to remedy this deficiency. As noted above, some telemetry systems allow a "wireless" distance to be placed between a health measuring unit and a remote monitoring system. However, such systems are limited in their range.

Other systems have used cellular telephone technology to increase the wireless health monitoring range. However, these systems have several deficiencies, such as requiring significant modification of the mobile phone. For example, U.S. Pat. No. 5,772,586, issued Jun. 30, 1998 to Heinonon et al., discloses a method for monitoring the health of a patient. This system uses a specialized connection between the patient health measuring unit and the cellular phone, however. The patient health measuring unit is located in the battery space of the mobile phone and is connected to a communication bus of the mobile phone. Other systems have been proposed, but these suffer from similar deficiencies in that they require specially modified cellular phones to be employed.

The deployment of the above systems also currently lacks employment of full back-end server functionality with which to provide a wide range of interactive communication with the patient. Instead, such systems, if internet-enabled, are often limited to mere one-way non-interactive data transfer via a modem.

SUMMARY OF THE INVENTION

Embodiments of the present invention overcome one or more of the disadvantages of the prior art by providing a full-feature health and exercise monitoring system that may wirelessly connect to a back-end server application via the internet. The invention allows wireless access to and from a wide variety of present exercise or health-related instruments and devices, while maintaining the capability of connecting to future such devices.

The advent of multimedia mobile phones and other personal communications devices that include a digital camera, or are able to connect with one, allows the capture and transmission of health and exercise information, including images. In embodiments of the present invention, multimedia mobile phones are used to transmit voice and images as well as data from an exercise monitoring device. In addition to the uploading of images, the display screen of a wireless internet device ("WID"), such as a smart phone, is used to allow the display of images such as illustrations, diagrams or video clips which may be downloaded from a server as part of an interactive user interface (e.g., for the purpose of describing to a user how to set up an exercise regime). The ability to include images in a system that is based on a WID connected to a exercise monitoring device helps facilitate the remote analysis and monitoring of exercise, fitness, nutrition, or health.

The reviewer or provider of exercise or health information is understood to include not only the user but also a trainer, coach, specialist, caregiver, physician, another user, or a software application or algorithm that may analyze the information. The information can include data from a variety of monitoring devices and images relating to the condition of the user. The images could include photographs or videos of the user's specific situation that could aid their exercise regime.

In particular, the invention may be embodied in several systems. Two complementary such systems are described herein, although extensions to other such systems can be envisioned. In the first embodiment, a health or lifestyle management plan may be implemented. Various exercise parameters, such as those relating to fitness, nutrition or exercise, may be received from an exercise monitoring device, and the same may be wirelessly communicated to a server. The exercise parameters may include physiological data, such as heart rate, blood pressure, respiration, or temperature; or data corresponding to the amount of exercise performed, such as number of miles traveled, how much work performed, or the like. In some cases, derived data, such as number of calories burned, may also be measured by an appropriate calculation. An application may process, store, and perform calculations on the exercise parameters, these may be reported back to the user, and a health, nutrition, or fitness specialist or other reviewer may optionally review the same or different derived or measured values. The second embodiment of the invention may be employed to manage the disease state or condition of a patient. In this embodiment, the patient, or a caregiver, may employ a health monitoring device ("HMD"), in particular a medical device, and a wireless connection to provide data from the medical device for processing via the internet, including a review by a physician or other health care professional if required.

In other embodiments, the condition of subjects may be evaluated by collecting exercise, health, or medical data and providing information in response to those data by means of a WID designed to display interactive information through a connection to the Internet. The present invention may be connected to various HMDs, and may communicate information via a wireless connection such as a wireless Internet connection. The user of the present invention may be the subject, or another person such as a trainer, coach, or physician. Wireless internet connectivity has many advantages. For example, in the first embodiment, a person interested in tracking an exercise program may take the WID to the local health club and attach the same to an exercise machine, send data output from various exercise machines over the Internet, which may include data relating to how much exercise or work was performed, and physiological data such as heart rate, and receive a personalized response from an application program running on a server. The individual may input caloric content of foods eaten, and may further input caloric content of exercise performed. In this way, e.g., a person in a weight-loss program may see in great detail whether they are expending more calories in the form of exercise than the same individual is consuming in the form of food. Alternatively, in the second embodiment, a diabetic could connect a blood glucose meter to a WID away from home and download data to a Diabetes Management Company's server and, in response, receive guidance displayed on the screen (or by voice) about choices for the next meal.

In general, in the health management embodiment, the system may be employed to monitor the physiological status of a healthy subject while exercising, or performing other activities by receiving data from a variety of exercise monitors that provide physiological data and/or data corresponding to the amount of exercise or work performed. Exercise monitors that provide physiological data may include heart rate monitors, respiration rate monitors, blood pressure monitors, accelerometers, pedometers, body weight scales, body fat gauges, biofeedback devices, physiotherapy or chiropractic equipment, or the like, and the same may be separate devices or devices incorporated within an exercise machine. Exercise machines may include, e.g., treadmills, rowing machines, steppers, other aerobic or anaerobic exercise equipment, weight machines, or any other type of exercise machine. Exercise data corresponding to an amount of exercise performed may be measured by such machines and sent to the WID as described. For clarity, such devices are termed herein "exercise monitors" or "exercise monitoring devices" and the same measure "exercise parameters" or "exercise data". Exercise parameters or data may include the above physiological data and/or data corresponding to an amount of exercise or work performed.

In more detail, embodiments of the present invention provide a method and system for assisting subjects to maintain a healthy lifestyle by collecting and transmitting exercise data and in turn receiving information in response to those data by means of a WID designed to display interactive information through a connection to the Internet. The present invention may be connected to various HMDs, both medical and exercise-related in nature, and may communicate information via a wireless connection such as a wireless Internet connection.

A major advantage of embodiments of the invention is that the same frees the patient from the constraints of wired systems. The same allows users with consumer "off-the-shelf" wireless devices, e.g. mobile phone, to significantly extend the range of connectivity over that of wired computers, or even wireless telemetry systems.

The WID may be a web-enabled mobile phone. Alternatively, the WID may be a PDA, palm, handheld, tablet, netbook, or laptop computer, equipped with a wireless modem. Besides these, the WID may be a hybrid device that combines the functions of a computer, PDA and telephone in some fashion. It should also be noted that the WID may be a web-enabled mobile phone or hybrid device using a satellite communications network.

In a separate embodiment, an adaptor is used if necessary to convert the output signal of the exercise monitoring device to a suitable input signal for the, e.g., WID. The adaptor allows connection of the WID to an exercise monitor, either separately or one that forms part of an exercise machine or other variety of health care equipment, and the connection may be made via several techniques.

As for wired techniques, a standard parallel bus, universal serial bus (USB), Firewire, serial cable, or similar industry-standard connection may be used if the input/output ports between the HMD and the WID are appropriate. Otherwise, a suitable separate adaptor may be employed.

The connection may also be an input such as a memory device reader, a disk drive or other media input for input of data, a USB port or phone jack or other such wired input, again employing an adaptor if required.

As for wireless techniques, infrared (IR), microwaves, radio frequency (RF), a variety of cellular protocols, a variety of 802.11 protocols, 802.15 protocols, 802.16 protocols, 802.20 protocols, other IEEE 802 family protocols, short range wireless transmission, wide area network or broadband transmission methods, such as Bluetooth®, wireless universal serial bus protocols (W-USB), WiFi, WiMax, WiFiMax, Long Term Evolution (LTE), ultrawideband protocols (UWB), Voice over IP (VOIP), or satellite communication protocols or other wireless protocols, or optical techniques including lasers, may be employed. As above, an adapter is used if necessary to convert the output of an exercise device to a suitable wireless signal for the WID, for example, a Bluetooth® virtual serial cable.

The user, or other person such as a trainer, may also input data manually, such as by a stylus, keypad, touch screen, synchronization from a PC, or by various other techniques discussed below. Such a capability may be especially useful for the input of food data, e.g., caloric content consumed, or the like.

A major advantage of the invention is that by use of an optional adaptor, the system is compatible with current and prior HMDs as well as maintaining a capability of adapting to future such systems.

A digital camera may be integral to the WID to provide photographic or video images to supplement the data from the HMD. Alternatively, the WID may be connected to a camera either through a wired or wireless connection. The HMD may also provide image data (e.g., exercise machine on-screen signals could be transmitted visually if an output connection is not available).

The interaction between a WID and a back-end server may provide a major additional advantage in certain embodiments of the invention. In particular, the relatively small amount of memory currently provided on a WID as compared to a back-end server limits the functionality of applications running on the WID, especially in terms of computing capacity, processing power, and user interface. By providing significant application functionality on the back-end, less memory and processing capabilities become necessary on the WID (i.e., on the "front-end"). Thus, memory may be used in the WID for an enhanced user interface or for other purposes, according to the user requirements. The invention is protocol-independent.

In a method according to an embodiment of the invention, the user connects to a specific Internet site and a software program, resident on a computer readable medium such as a hard disk drive, flash memory, permanent disk storage such as a DVD-ROM, firmware, or the like, on a remote server located on the Internet, downloads an interactive user interface for that patient or subject user and an application for the measurement of the exercise information or that allows, enables, controls, or otherwise provides for the transfer of information from the exercise monitor to the WID. Alternatively, the software may have been previously installed on the WID by a supplier or a from a memory device, or downloaded to a computer readable medium of the WID such as an internal memory storage, or in another manner as is known in the art, from a personal computer or wireless access point or via other wireless download technologies via a synchronization operation in known fashion.

The software provides a personalized display for the user and configures the WID to control and monitor devices connected via a generic input/output port to the WID. The software may be designed to suit the constraints of the small display screens of WIDs. The software, as well as inputs from the user or other inputs, can control the manner, content, and display of information presented to the user, and measured or input data can be stored for review by the user, a trainer, coach, health care professional, other user, or be processed further by a software algorithm or application. The algorithm may be of varying complexity, from a simple program that merely provides a response to the user, to an artificial intelligence algorithm, such as an expert system, collaborative filtering system, rules-based system, case-based reasoning system, or other such artificial intelligence application.

Further information may be provided to or from the user, including information entered manually, e.g., calories consumed or exercise performed. The user may input this information directly on the WID or via a personal computer, which then may download the input information to the WID via a synchronization operation using standard protocols, such as those for smart phone devices.

The user may also input supplemental information via a PC connected independently to the server via the internet. Alternatively, the user may input this information via a connection with another device using standard protocols, wired or wireless connections including a variety of 8021.11 protocols, a variety of 8021.15 protocols, a variety of 802.16 protocols or wireless transmission methods such as Bluetooth®, WiFi, WiMax, WiFiMax, or infrared wireless connections. In addition, a Global Positioning System (GPS) device can be used to provide data about the location of the user. The GPS information can be used to calculate an exercise parameter corresponding to the amount of exercise performed, e.g., by tracking the distance traveled.

The use of a WID equipped with a "hands-free" earpiece and microphone allows the user to interact with the trainer, coach, or health care professional while recording exercise data. The use of a camera-equipped mobile phone further allows the trainer or health care professional to instruct the user to send photographs or video to assist in the exercise performance or analysis. The deployment of voice processing technology may be used to allow an even more convenient user interface.

In all of these respects, the portable aspect of the WID is important: to wit, the user may conveniently carry the WID on their person wherever they go, allowing data entry at the time needed or as is convenient. A wearable WID such as implemented by a smart watch, eyewear, article of clothing, or other device or configured to be worn by a person, makes it even more convenient for a user to carry the WID on their person.

A, trainer, coach, or other person reviewing the data may also input supplemental information via a PC connected independently to the server via the internet to supplement the data input to the WID. Such supplemental information may include data that is not otherwise available to the user.

Other aspects, features, and advantages will be apparent from the summary above, as well as from the description that follows, including the figures and the claims.

DETAILED DESCRIPTION OF THE PREFERRED EMBODIMENTS

Figure 1:
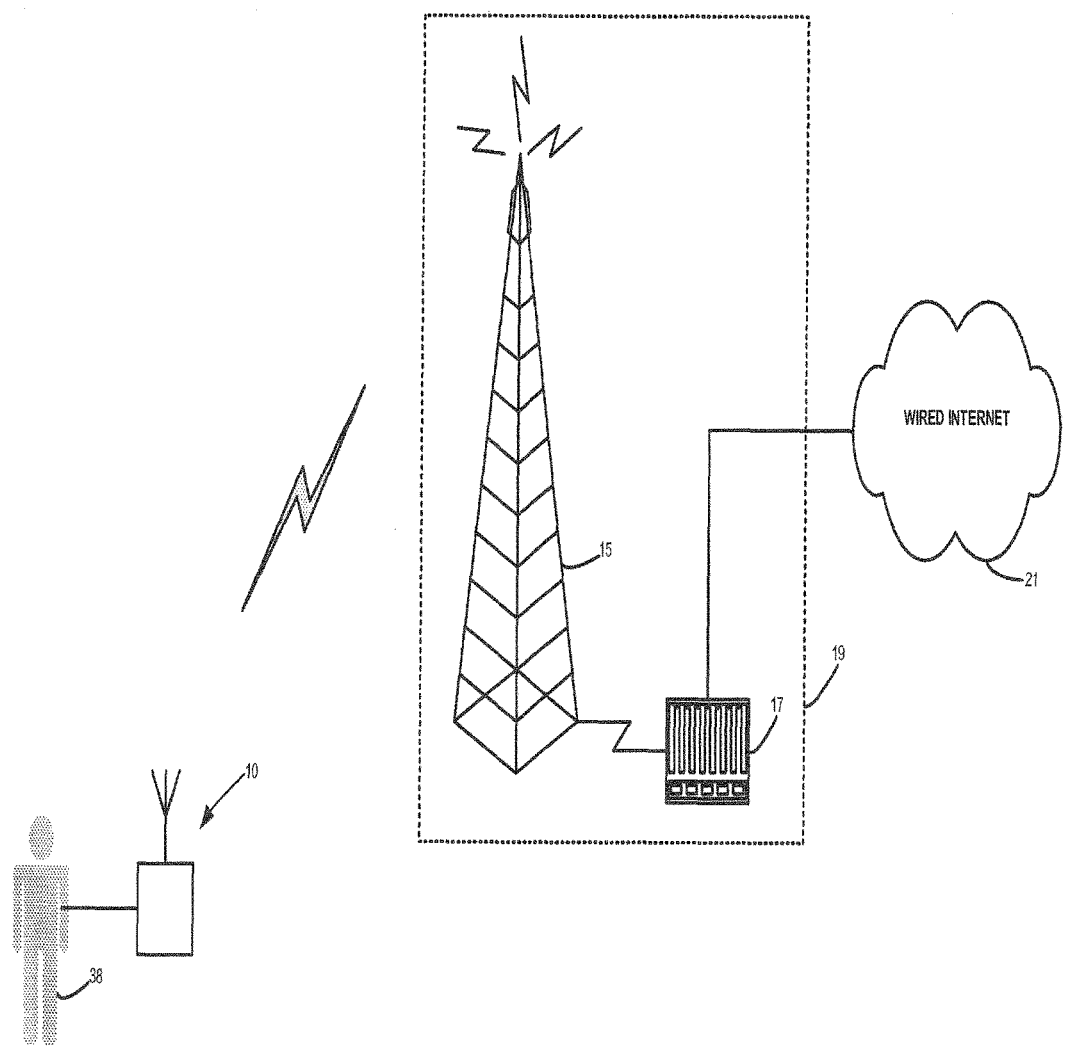
FIG. 1 illustrates a general embodiment of a wireless health-monitoring system according to the present invention.

Various acronyms are used for clarity herein. Definitions are given below. The term "HMD" may encompass not only devices with physiological and exercise data sensors but also devices with a keypad, keyboard, mouse, touch screen, pointer, pressure sensor, or other such inputs that the patient or user may employ to perform data entry of the desired parameters. In general, HMDs include some means for determining an exercise or health parameter. For receiving physiological data, an HMD may be a heart rate monitor, a blood pressure monitor, an ambulatory ECG recorder, a respiratory monitor, a temperature monitor and so on.

For receiving exercise data corresponding to the amount of exercise performed, an HMD may be an exercise monitor such as a pedometer, accelerometer, biofeedback device, or other sensor tracking duration, rate, intensity or total amount of exercise, such as number of miles traveled. In a healthy lifestyle management embodiment, an HMD may be incorporated within an exercise machine, including treadmills, rowers, steppers, exercise cycles, or other aerobic or anaerobic exercisers, the same providing exercise data corresponding to the amount of exercise performed such as number of miles traveled, duration of exercise or rate of work performed, and the same may provide physiological data such as heart rate, and additional derived data such as the number of calories.

The term "subject" as used herein primarily indicates a human subject. The same may be, a person interested in maintaining health via accurate recording of exercise, fitness, and nutrition, and so on, or a medical patient under a physician's care or the care of another healthcare professional The term "user" is generally used to refer to a user of the WID, which may be synonymous with the subject or may alternatively be another person using a similar WID to review the data from the first user. A user may also be a trainer, fitness coach, physician monitoring an exercise program, or the like. The term "patient" is used, in addition to a person under the care of a physician, to also refer to a "normal" or healthy individual who is interested in maintaining a healthy physiological balance.

The term "signal communication" is used to mean any type of connection between components where the connection is, e.g., electromagnetic, and where the connection allows information to be passed from one component to another. This term may be used in a similar fashion as "coupled", "connected", "information communication", "data communication", etc. The following are examples of signal communication schemes. As for wired techniques, a standard USB or serial cable may be used if the input/output ports are compatible and an optional adaptor may be employed if they are not. As for wireless techniques, examples of employable techniques include: infrared (IR), microwaves, radio frequency (RF), a variety of cellular protocols, a variety of 802.11 protocols, 802.15 protocols, 802.16 protocols, 802.20 protocols, other IEEE 802 family protocols, short range wireless transmission, wide area network or broadband transmission methods, such as Bluetooth®, wireless universal serial bus protocols (W-USB), WiFi, WiMax, WiFiMax, Long Term Evolution (LTE), VOIP, ultrawideband protocols (UWB), satellite communication protocols or other wireless protocols, or optical techniques including lasers. The user may also input data manually, such as by a stylus or keypad, touchpad or by various other techniques discussed above and below.

The term "generic input/output port" is used to mean any type of conventional, standard, universal, stock, consumer, or "off-the-shelf" port for data input and output. These may include both wired and wireless ports and may be located externally or internally to the WID. A further description is given below.

Various embodiments of the invention are now described in more detail.

Referring to FIG. 1, a system is shown for monitoring exercise data from a patient or subject 38. The system includes a wireless exercise monitoring apparatus ("WEMA") 10 described in further detail below. WEMA 10 is linked in a wireless fashion to a wireless connection point of presence ("POP") 19, the same including at least a base station antenna 15 coupled to a server 17. Server 17 is in turn connected to the wired, or even a wireless (not shown) Internet 21, which may include the World Wide Web.

It should be noted that the base station embodiment shown in FIG. 1 may be replaced or removed for mobile phones which connect via satellite i.e., "satellite phones", rather than via a cellular network or other wireless communication.

Figure 2:
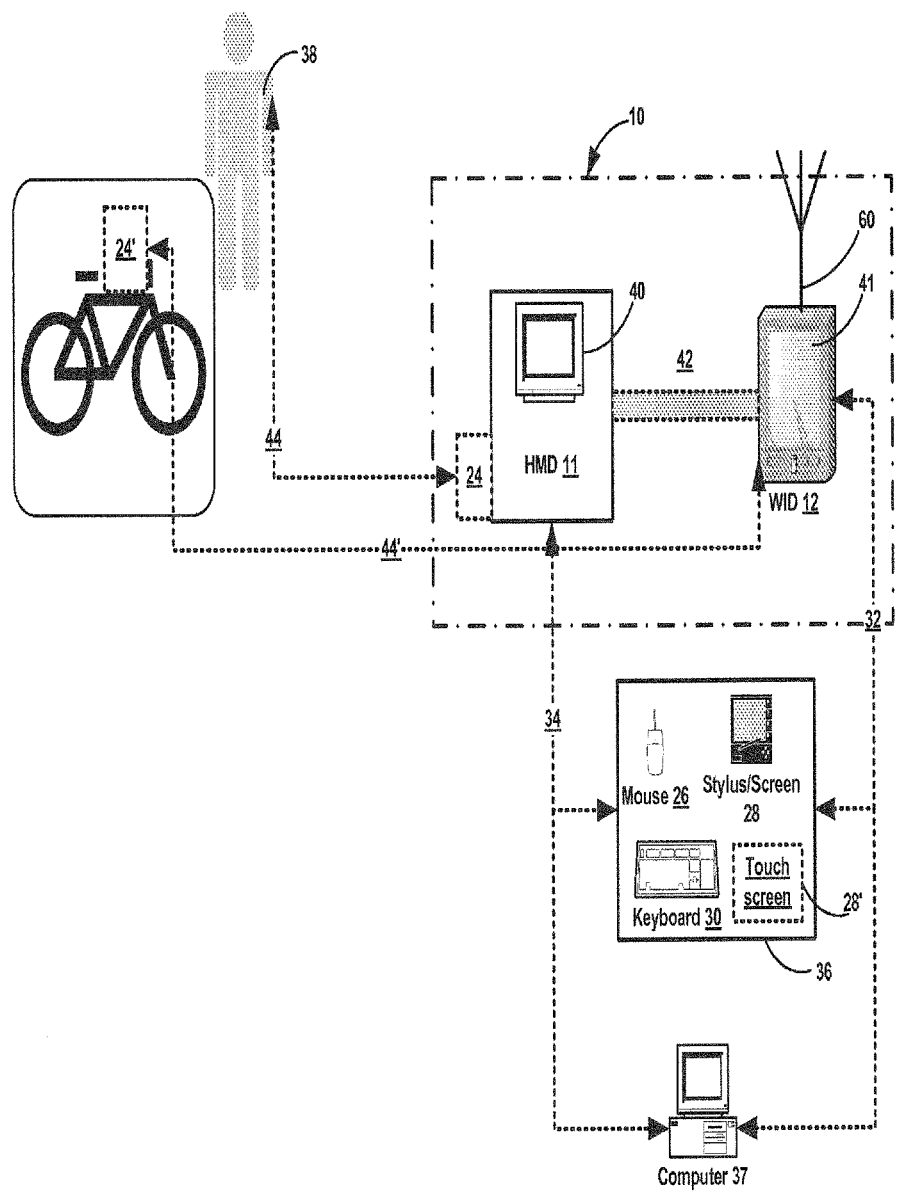
FIG. 2 illustrates an embodiment of a wireless health-monitoring apparatus according to the present invention, showing the system of FIG. 1 up to a point of a wireless antenna 60.

Referring to FIG. 2, a first embodiment of WEMA 10 is shown. WEMA 10 includes an HMD 11, which may include an optional monitor screen 40, coupled via an optional adaptor 42 to a WID 12. WID 12 connects wirelessly via an antenna 60 to base station 15 (see FIG. 1). One function of WID 12 may be to provide the user interface; other functions are described below.

As noted above, HMD 11 may include a physiological sensor 24 which connects to the HMD via a connection 44 (or which may alternatively connect directly to the WID) or a sensor 24' tracking an amount of exercise performed that connects to the WID (or HMD) via a connection 44'; or may include a manual system 36 for input of physiological and exercise data via a connection 34. Manual system 36 may also be used to input data directly into WID 12 via a connection 32. Manual system 36 may include, e.g., a keyboard or keypad 30, a mouse 26, a pen-type device 28, touch screen 28' and may also employ a separate monitor (not shown). Of course, the user may also view information on monitor 40 or on a screen 41 of WID 12. In many embodiments, the touch screen or keypad system employed by many current mobile phones such as the iPhone®, may be preferred for such manual data input.

Data may also be input via entry on a computer 37. This data may then be synchronized to WID 12 in known fashion. Alternatively, computer 37, or another computer may be used to connect to a server using the wired internet. This use may be particularly advantageous when entering a large amount of data. As noted above, in this way the user may be afforded a more convenient environment in which to manipulate data to supplement the data input to the WID.

It will be clear to one of skill in the art given this teaching that cable 32, as well as cables 34 and 44, may be replaced with wireless circuitry to communicate signals wirelessly. Alternatively, cables 34 or 44 may be replaced by a direct plug and socket connection. In this connection, adaptor 42 may be a direct plug and socket connection.

For exercise devices and applications, physiological sensor 24 may include, e.g., a sensor appropriate for measuring heart rate, respiration, blood glucose levels, blood oxygen levels, blood pressure, electrocardiograms (ECG), or any other desired physiological parameter. Sensor 24 may also include a camera configured as a heart pulse monitor by detecting color or heat changes. Sensor 24 may connect via an optional cable 44 to subject 38. Alternatively, sensor 24 may be distal of HMD 11, i.e., at or within subject 38. In other words, if cable 44 is employed, sensor 24 may be proximal or distal of cable 44. In some applications, such as some types of cardiac monitoring, sensor 24 is implanted within the patient. The sensor 24' tracking the exercise performed may include, e.g. a pedometer, accelerometer, biofeedback device, timer, GPS device, or other sensor tracking duration, rate, intensity or total amount of exercise.

Either or both the physiological sensor and/or sensor tracking the amount of exercise may be incorporated in exercise machines such as a treadmill, exercise bicycle, stepper and so forth. Alternatively, other exercise monitors may also be employed so long as the measured data may either be transferred to WID 12, e.g., via optional adaptor 42, described in further detail below, or by being read by a user, e.g., from a display, and manually input to the WID.

If a wireless communications capability is added, sensor 24 or sensor 24' need not physically connect with HMD 11 or WID 12 at all. That is, the same may measure an exercise parameter and may communicate the same to WEMA 10 wirelessly. The short-range wireless communications schemes which may be employed include infrared, radio frequency including a variety of 802.15 protocols such as Bluetooth®, a variety of 802.11 protocols such as WiFi or any other such wireless transmission schemes, including those described above.

As examples of sensor types, to measure heart rate, sensor 24 may be placed via a chest band or an adhesive sensor disposed on the chest. As an example of sensor type 24' to measure the amount of exercise performed, a pedometer may be disposed on the user to track the number of miles traveled. Other exercise monitors may also be employed so long as the measured data may either be transferred to WID 12, e.g., via optional adaptor 42, described in further detail below, or by being read by a user, e.g., from a display, and manually input to WID 12. Alternatively, the measured data may be transferred to WID 12 via wireless communication schemes, using a variety of 802.15 protocols such as Bluetooth®, a variety of 802.11 protocols such as WiFi, infrared, optical, microwaves, etc., directly from sensor 24 or sensor 24' or from HMD 11 as described in greater detail below. HMD 11 may be a wearable device, such as a watch in wireless communication with sensor 24, e.g. a heart rate chest band; or sensor 24 can be integrated with the watch, e.g. a resident pulse monitor. Sensor 24 may also be integrated in an article of clothing, e.g. smart apparel. The wearable device may communicate wirelessly with WID 12, e.g. a mobile phone, or with the Internet 11 directly via other transceiver means.

The user, who may or may not be the same person as subject 38, may input data to WID 12 to supplement the measured data. For example, in a health or exercise system, if subject 38 consumes a known number of calories, this information may be entered via manual system 36 directly into WID 12 or into HMD 11. Further, the user, the subject, and the sensor are not necessarily the sole sources of information. Data stored on the server, or on a separate server operated for health management, may also be employed to result in a health benefit to subject 38.

Figure 3:
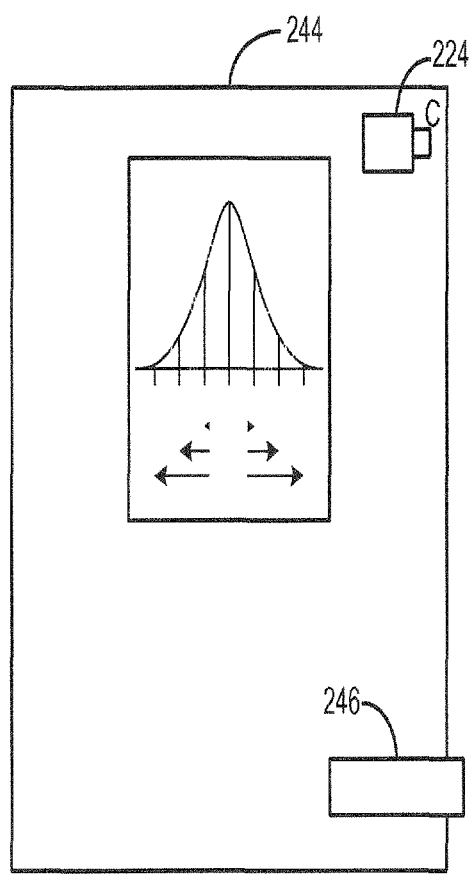
FIG. 3 illustrates an embodiment of a WID employing a camera, which may be integral or not.

The data used to benefit the subject 38 may be from a camera as well as from an HMD. Referring to FIG. 3, an embodiment of a WID 244 is shown equipped with a camera 224 and an optional memory device 246. The camera may be integral to the WID, or may be separate and connected via a cable. The camera may be incorporated in a wearable WID, e.g smart Particularly important types of visual data about a user that may be wirelessly transmitted from the WID are those corresponding to photographic pictures, both still and video, and graphical or visual data output images from an HMD, e.g., an exercise machine. In either case, a trainer, coach, or medical personnel may use such data to take appropriate action.

To obtain the first type of data noted above, photographic data, a camera may be employed, which is either resident on the WID or is otherwise available by way of a wired or wireless link. The WID may store photographic data, either still or video, and transmit the same wirelessly to a point of collection, e.g., a server application, or may save the photographic data on the memory device or in other device storage for contemporaneous or later transmission, again either via a streamed, non-streamed, or other transmission method. The WID may be in the form of a wearable device equipped with a camera, e.g. eyewear or watch. As noted above, the WID may connect with a physiological sensor 24, e.g. a distal or integrated pulse monitor, and with a sensor 24' to measure the amount of exercise performed, e.g. a distal or integrated GPS device.

There are various ways in which visual data may be communicated to a remote reviewer. A simple method is to send the visual data via an email message. In more advanced methods, the visual data may be integrated with a data stream of other medical information. Current systems may be used in combination with the present invention to facilitate the handling and transmission of visual data by a WID. In all cases, the visual data may be stored, e.g., as a separate file or may be included as an embedded object in a data file on the memory device or in an email.

In more detail, a data port from a HMD that is coupled to a user may be employed to send visual information from the same to an input port on the WID. This transmission may be accomplished via the techniques described above. Such data may be in either a raw form or in a preformatted-for-video form, and may be stored in the WID or on the memory device. In either case, it may be required to format the data in a way suitable for the display screen of the WID. In some cases, viewing on the WID is not necessary, and the data may be sent in its original form, optionally undergoing some intermediate processing, directly on to the trainer, coach or other remote reviewer's system for viewing or analysis. Examples of this type of data may pertain to the performance of exercise data or other sources of data. The remoter reviewer may include another user, similarly equipped with a WID, e.g. when the users are engaged in team activities.

Alternatively, a subset of the data may be sent, such as a compressed version, while the remainder, i.e., the complete version of the user data, may be maintained on the WID and/or memory device for purposes of maintaining a complete user record.

The memory device 246 may be a smartcard, a smartmedia card, a memory card, memory stick, compact flash card, memory cubes, micro-drives, disk-on-keys, flash memory-keys, micro-laser disks, nano-storage devices, bio-memories, battery/memory combination device, USB flash drives, and so on, or indeed any other type of removable media that may be connected to a WID to store information. Typically, these memory devices are capable of storing substantial amounts of data. The same may also include a memory and power source or combination device. In another embodiment, the memory device 246 may be inserted (not shown) in a memory device reader, which is in turn connected to a WID via a link.

Of course, in some devices, including some current smart mobile phones or other wireless mobile devices such as netbooks, there is no need for a separate memory device 246 as the internal storage capacity, e.g. in the form of solid state memory, microdrive or other memory storage devices, is sufficient to store all applications and data. Whether via a memory device 246 or internal storage, enhanced functionality and storage are provided for the WIDs 244 or 250. This may be particularly important for exercise data, as certain physiological monitoring apparatuses produce copious amounts of data, e.g., cardiac monitoring equipment, and thus require substantial storage capabilities. This is particularly true for memory-intensive video and multimedia content.

Another reason such memory devices are particularly pertinent in medical device monitoring is that they store data which can then be wirelessly transmitted in a streamed or non-streamed fashion. In the event of drop-outs, interruptions, or unavailability of the wireless network, no loss of data occurs, as the data has been stored on the memory device and may be wirelessly transmitted at a later time when cellular or mobile service is again available. The memory device thus serves as a backup storage media. In the event of an extended period of unavailability of a wireless network, the memory device may be replaced or overwritten to provide practically unlimited storage until such time as the network is available and the data can be uploaded. In more detail, in the case of a dropout or other disruption of wireless service, the data may be stored on the memory device or in the WID if it has not already been, as may be the case for streamed data. The WID may periodically test for the availability of the wireless network, and may wait until the network is available. Once the system is again available, the advice from the trainer, coach or other reviewer may be sent to the WID and the user may again take action.

Of course, even if the wireless network is available, the memory device or on-board WID memory may store the data for various purposes. This real-time capability and robustness is often very important in ensuring user safety and ensuring that a high level of care is being delivered to the user by the trainer, coach, or medical personnel, particularly in field situations, such as running or, bicycling, where the wireless connection may be the only source of communication. A related reason why memory devices are particularly pertinent in exercise device monitoring is that they allow a greater level of buffering for real-time data monitoring, thus allowing more pre-analysis and filtering of data.

A further benefit of the use of memory devices is that they provide for easy application downloading onto a WID. For example, a memory device may be inserted into a WID and a large application program may be easily downloaded onto the computer-readable media of a WID from the memory device rather than through a wired or wireless synchronization or downloading process via a PC or the internet or both. Appropriate types of computer-readable media have been described above. Downloading in this fashion may be particularly rapid and complete. The downloaded data may include visual data, such as still or video photographic images, that instruct a user on the operation of a device. In an alternative embodiment, visual data need not be downloaded but may rather be streamed, either from a stored video on a server or in real-time via a user with a webcam. In downloaded or streamed but generally not live systems, the user interface may be interactive, allowing the user to access a knowledge database resident on the server or memory device or previously downloaded onto the memory of the WID.

Figure 4:
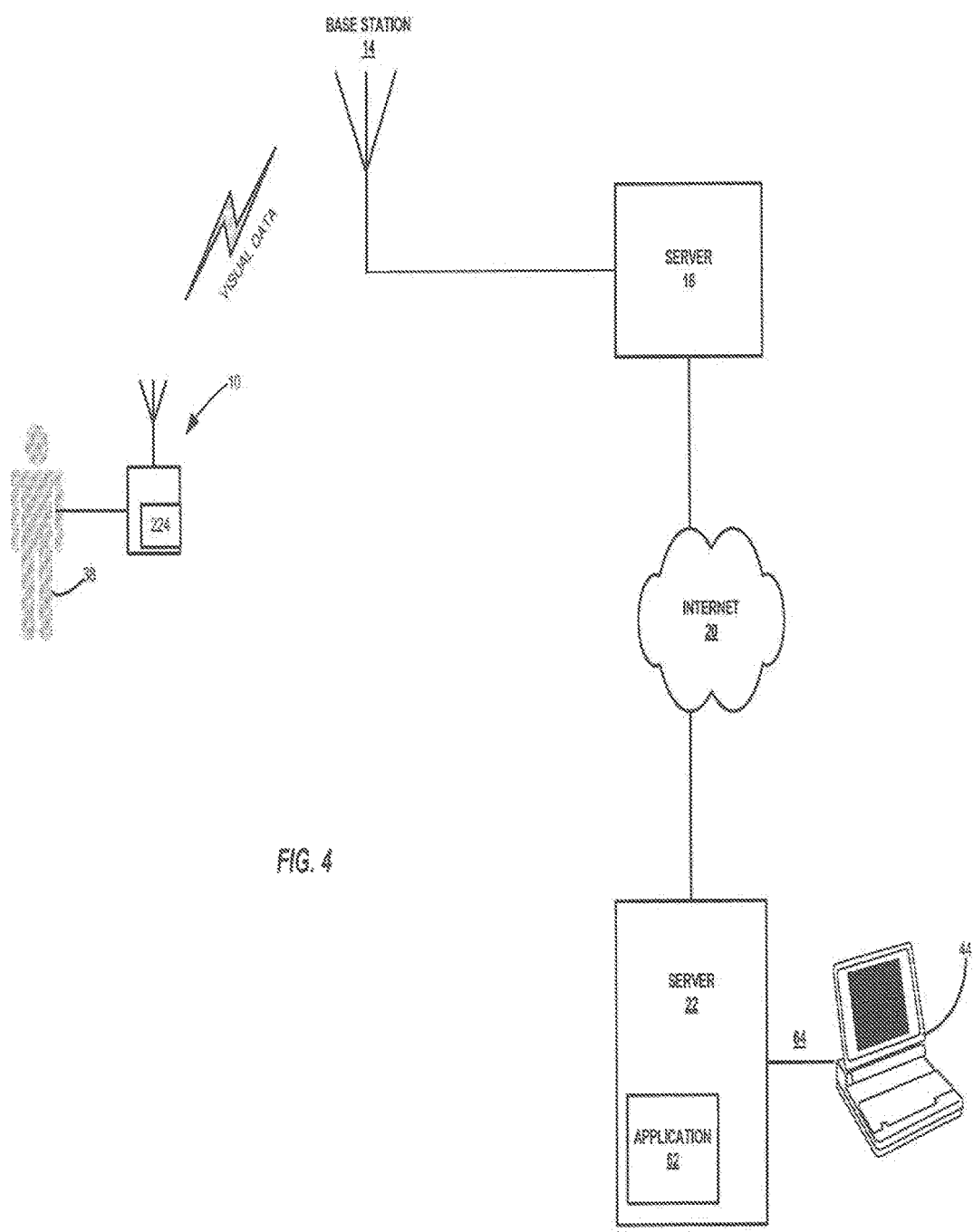
FIG. 4 illustrates an embodiment of a back end of an exercise monitoring system according to the present invention.

Referring to FIG. 4, WEMA 10 is shown communicating wirelessly with the Internet. In doing so, WEMA 10 generally sends a wireless signal to a base station 14 (in known fashion) that is connected to a server 18 that is in signal communication (in known fashion) with the internet 20. Server 18 communicates via a protocol (in known fashion) to Internet 20, which also communicates via a protocol (in known fashion) to a server 22 running an application 62. Server 22 may be accessed (in known fashion) by a client computer 44 through a connection 64.

As noted, the protocols for data communication are known. They include a variety of cellular protocols, a variety of 802.11 protocols, 802.15 protocols, 802.16 protocols, 802.20 protocols, other IEEE 802 family protocols, wide area network or broadband transmission methods, WiFi, WiMax, WiFiMax, Long Term Evolution (LTE), VOIP, ultrawideband protocols (UWB), or other wireless communication protocols, and may include a satellite instead of ground-based communication systems. However, they currently vary amongst known techniques. The present invention is not limited to any particular protocols, and may be implemented in any languages supported by the WID and server. In particular, the wireless communications schemes envisioned by the present invention include cellular, mobile, satellite, and other such wireless techniques. In such wireless communication systems, an additional security layer may be employed, including industry-standard encryption and decryption of the transmitted data, especially as health information is highly sensitive and private data.

Of course, as computing capabilities continue to increase, it is expected that the capabilities of WEMA 10, servers 18 and 22, as well as application 62 and client 44, and other components, will correspondingly increase.

Figure 5:
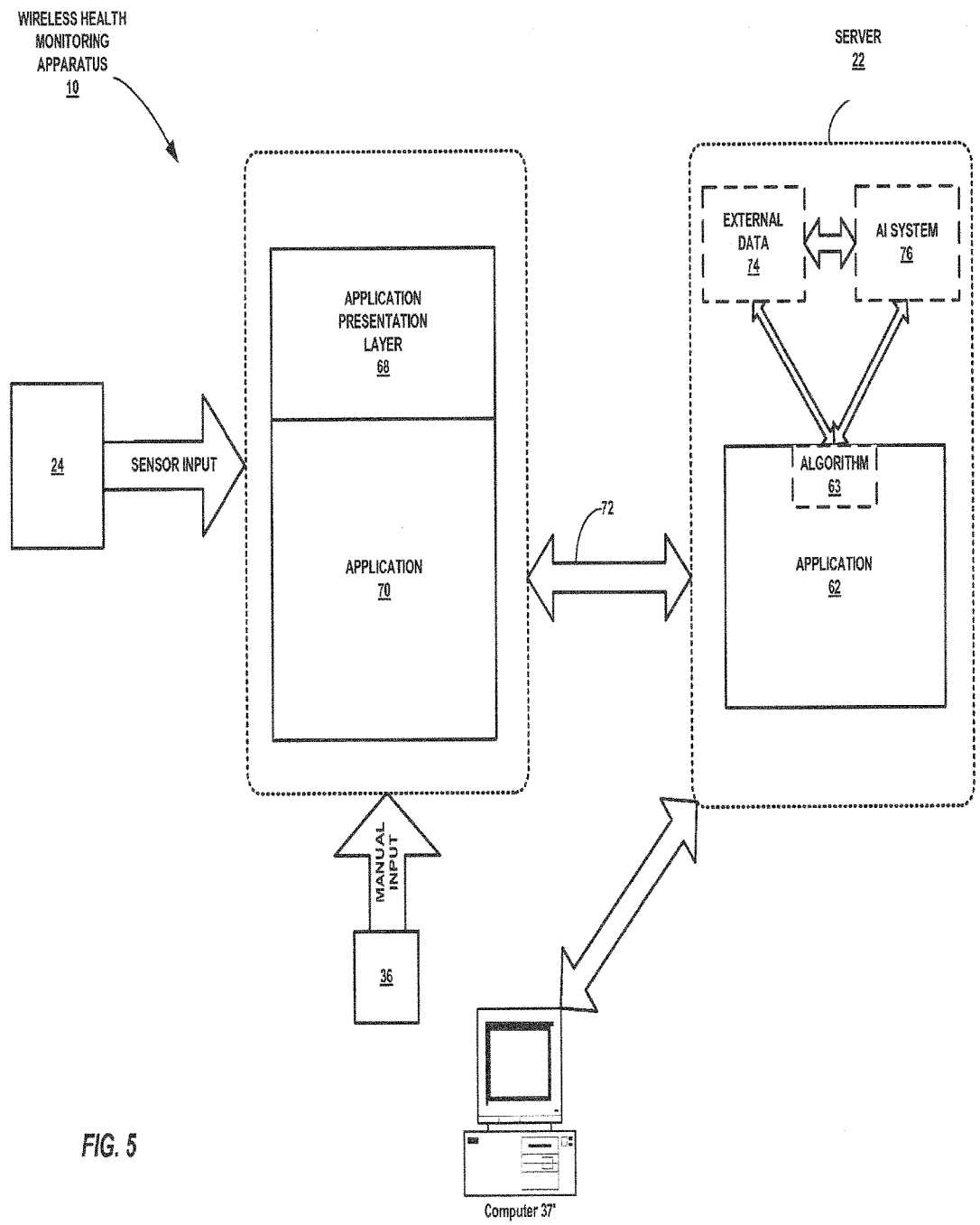
FIG. 5 illustrates a data flow diagram according to an embodiment of the present invention.

Application 62 running on server 22 which is stored in computer readable media as described above may interact with WEMA 10 in a number of ways. Referring to FIG. 5, WEMA 10 is shown in signal communication with server 22 via a connection 72. Connection 72 schematically represents the wireless Internet connection and intervening pathways. WEMA 10 includes an application that may be viewed as having two components: a base wireless or device application 70 and an application presentation layer or user interface 68. User interface 68 is employed to, e.g., present a menu of options to the user, to allow the user to choose inputs, and to generally operate the device. User interface 68 may vary widely in sophistication, e.g., from a simple data entry field to a full graphical user interface. These applications may accept as inputs data from a sensor 24 and sensor 24' as well as from a manual input 36.

Server 22 has a base server application 62 stored on computer-readable media as described above with which the same calculates or provides a response based at least in part on data from WEMA 10. Application 62 may include an algorithm 63 for analyzing data from the HMD, and either application 62 or algorithm 63 may optionally access data from an external data source 74 and may further consult an artificial intelligence system 76. Server 22 may be accessed by a remote computing device 37' by the subject user, a trainer, coach, or any other reviewer.

External data source 74 may be a memory or disk or other such storage that stores health data, such as healthy and unhealthy weight/height ranges, healthy and unhealthy cholesterol counts, the user's prior medical or health history, healthy and unhealthy heart rate values, information corresponding to the caloric and other nutritional content of foods, information corresponding to the caloric expenditure values of various exercises, algorithms for calculating various health parameters, etc. In general, any data that may benefit the health of a user may be stored in external data source 74. External data source 74 may be a memory device or other such storage that stores supplemental data such as treatment protocols. In general, any data that may benefit or otherwise affects the health condition of a user may be stored in external data source 74. External data source 74 may also include online access of health information from external databases or other sources.

As noted, application 62 or algorithm 63 may also consult AI system 76 for suggestions as to health benefits. AI system 76 may even interact with external data source 74 to extract useful information from the same. AI system 76 may employ, e.g., case-based reasoning, rules-based systems, collaborative filtering, neural networks, expert systems, or other such systems as are known.

It should also be noted that each of application 62, algorithm 63, external data source 74, or AI system 76, may physically reside on more than one server, e.g., on an array of servers for, e.g., storage or multiple processing purposes. Each of application 62, algorithm 63, external data source 74, or AI system 76, or combinations of each, may also respectively reside on different servers.

The extent to which server application 62 interacts with wireless application 70 depends on the use to which the system is put. For example, in a less interactive embodiment, device application 70 may act to measure a user's heart rate during exercise and report the same to server application 62. In this case, a trainer may simply review the measured value and send the user a response reporting that the value is acceptable or not. In a highly interactive embodiment, a user may have numerous HMDs 11 measuring a variety of physiological data and/or other data tracking the amount of exercise performed, connected via optional adaptors to a WID 12, and wireless application 70 may correspondingly send a large amount of exercise data to server application 62. The trainer, coach, or physician accessing server application 62, may in turn send detailed plans for an exercise regimen via connection 72. The received data may be analyzed using algorithm 63, external data source 74, and AI system 76. In this sense, the two applications may be highly interactive.

It is noted that an Application Service Provider (ASP) may operate application 62. That is, application 62 may be leased by an ASP to a company specializing in fitness or lifestyle management, and the ASP may perform all necessary upgrades and maintenance to application 62 and its associated components.

To initialize the system, the program starts and a wireless application is loaded into computer readable media in the WID, if it has not been pre-loaded. The initial loading of the wireless application may occur via synchronization from a desktop or via downloading from a server over the internet. The server application may be loaded into computer readable media in an appropriate internet-connected server. Subject data may be loaded into the WID or into the server application. In the latter case, the subject information may later be transferred to the WID. The initialization scheme then ends.

The wireless application may access the server and server application, or vice-versa, as determined by the respective program instructions.

Figure 6:
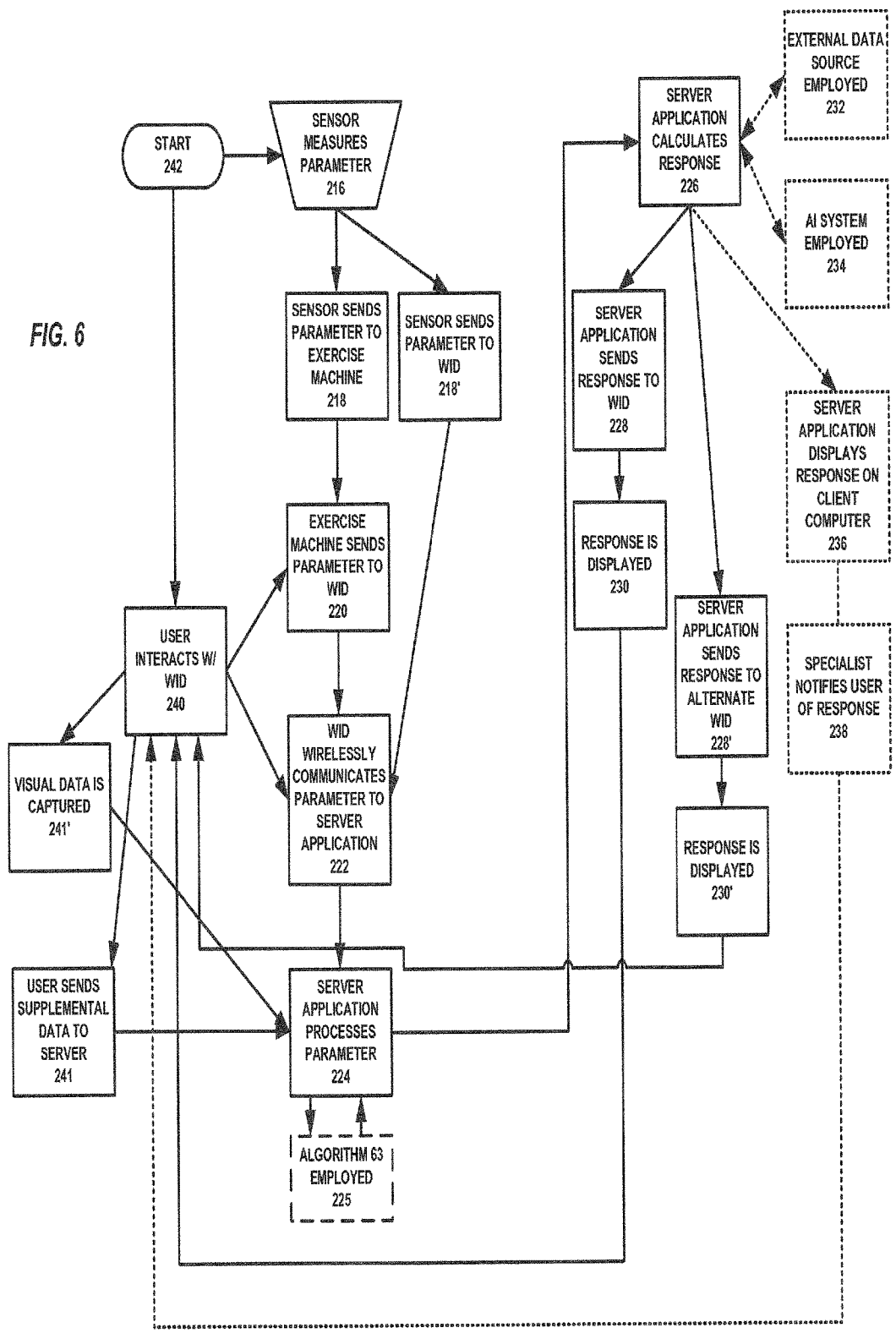
FIG. 6 illustrates an embodiment of a method of use for a wireless application and a server application according to the present invention, in which the same is implemented for exercise monitoring.

Referring to FIG. 6, a flowchart of a method is shown for a system of exercise, fitness, nutrition or health monitoring, and/or exercise management. In this example, the HMD is in the form of a general exercise machine such as a treadmill, stepper, exercise bicycle and so forth. An exercise monitor may be integral to the exercise machine or may be separate.

In the method, both exercise data and visual data may be wirelessly transmitted from the WID. Visual data include that corresponding to photographic pictures, both still and video, and graphical or visual data output images from an HMD, e.g., an exercise machine or equipment display screen, or other images related to the exercise being performed. A trainer or coach may review these images and use them to guide the user as appropriate as described below.

After the start (step 242) of the method, a user interacts with a WID (step 240). By the interaction, visual data may be captured (step 241'), and/or the user may send supplemental data to the server and server application (step 241).

To obtain the visual data noted above, photographic data, a camera may be employed, which is either resident on the WID (camera 224 of FIG. 3) or is otherwise available by way of a link. The WID may store photographic data, either still or video, and transmit the same wirelessly to a point of collection, e.g., a server application, or may save the photographic data on the memory device for contemporaneous or later transmission, again either via a streamed, non-streamed, or other transmission method (step 208 of FIG. 6).

Also after the program is started (step 242), a sensor measures an exercise parameter (step 216), where the exercise parameter corresponds to physiological data or to data corresponding to the amount of exercise performed.

The exercise monitor sensor may send the parameter to the exercise machine (step 218) or the parameter may be sent directly to the WID (step 218'). It is understood here that the "sensor" may pertain to any of the exercise monitors discussed above.

If the parameter is sent to the exercise machine as an intermediate step, the exercise machine then sends the parameter to the WID (step 220). In any case, the WID wirelessly communicates the parameter to the application server (step 222), e.g., via the wireless web.

An alternative and complementary way of entering the parameter is by user input. For example, the user may enter the parameter into the exercise machine or into the WID. This parameter may correspond to an amount of exercise performed, an amount of food consumed, etc. Such data and other types are termed supplemental data, and may be transmitted to the server and server application (step 241). Calculations by the server application may take into account the supplemental data as well as the visual data and exercise data.

The server application processes the parameter (step 224 and optionally step 225), and calculates a response (step 226) based at least in part on the parameter. The server application may optionally employ external data (step 232) or an AI system (step 234) in the calculation. The application server then sends the response to the WID (step 228), where the response is displayed (step 230). Alternatively, the application server may sends the response to an alternate WID (step 228'), such as that of a coach or teammate, where the response is displayed (step 230').

The same definitional statements regarding the terms "response", "calculate", "sensor", etc., as given before, apply in this embodiment as well.

As an optional step, a trainer, coach, or other specialist may notify the user of the response (step 238) after having the same displayed on their client computer (step 236). The specialist may be replaced in this example by an application that may also include an algorithm.

To devise the exercise data mentioned above, a data port from a HMD that is coupled to a user may be employed to send information from the same to an input port on the WID. This transmission may be accomplished via the techniques described above. Such data may be in either a raw form or in a preformatted-for-video form, and may be stored in the WID or on the memory device. In either case, it may be required to format the data in a way suitable for the display screen of the WID. In some cases, viewing on the WID is not necessary, and the data may be sent in its original form, optionally undergoing some intermediate processing, directly on to the remote reviewer's system for viewing or analysis. Examples of this type of data may be the display output of an exercise machine or other sources of data. Alternatively, a subset of the data may be sent, such as a compressed version, while the remainder, i.e., the complete version of the user's data, may be maintained on the WID and/or memory device for purposes of maintaining a complete user record.

The WID may store the HMD data, and transmit the same wirelessly to a point of collection or may save the data on the memory device for contemporaneous or later transmission, again either via a streamed or other transmission method. The memory device may be any type of computer-readable media, including, e.g., a smartcard, a smartmedia card, a memory card, memory stick, compact flash card, memory cubes, micro-drives, disk-on-keys, flash memory-keys, micro-laser disks, nano-storage devices, bio-memories, battery/memory combination device, USB flash drives, and so on, or indeed any other type of removable media that may be connected to a WID to store information.

In the case of a dropout or other disruption of wireless service, the data may be stored on the memory device or in the WID if it has not already been, as may be the case for streamed data. The WID may periodically test for the availability of the wireless network, and may wait until the network is available. Once the system is again available, the advice from the caregiver may be sent to the WID and the on-site personnel may again take action.

Using such data, an off-site trainer, coach, or other health care professional may give the user valuable guidance and advice. Moreover, no wired or dedicated connection is necessary.

More particularly, for visual data, there are various ways in which such data may be communicated to an off-site reviewer. A simple method is to send the visual data via an email message. In more advanced methods, the visual data may be integrated with a data stream of other information. Current systems may be used in combination with the present invention to facilitate the handling and transmission of visual data by a WID. In all cases, the visual data may be stored, e.g., as a separate file or may be included as an embedded object in a data file on the memory device or in an email.

Adaptor Hardware

A description is given below of a particular type of adaptor hardware. As noted above, the adaptor may optionally be used to connect a HMD to a WID.

In general, a connection is necessary between a HMD 11 and a WID. The nature of this connection may vary. For example, the connection may be wired or wireless. For wired systems, the connection may be direct or an adaptor may be employed, either on one or both ends of the direct wired connection, to adapt the signal appropriately. In the same way, for wireless systems, the connection may be direct, if both HMD and WID employ the same wireless protocol, or an adaptor may be involved to modify the signal of one or both devices. These connections, all of which are encompassed by the present invention, are discussed in more detail below.

Figure 7:
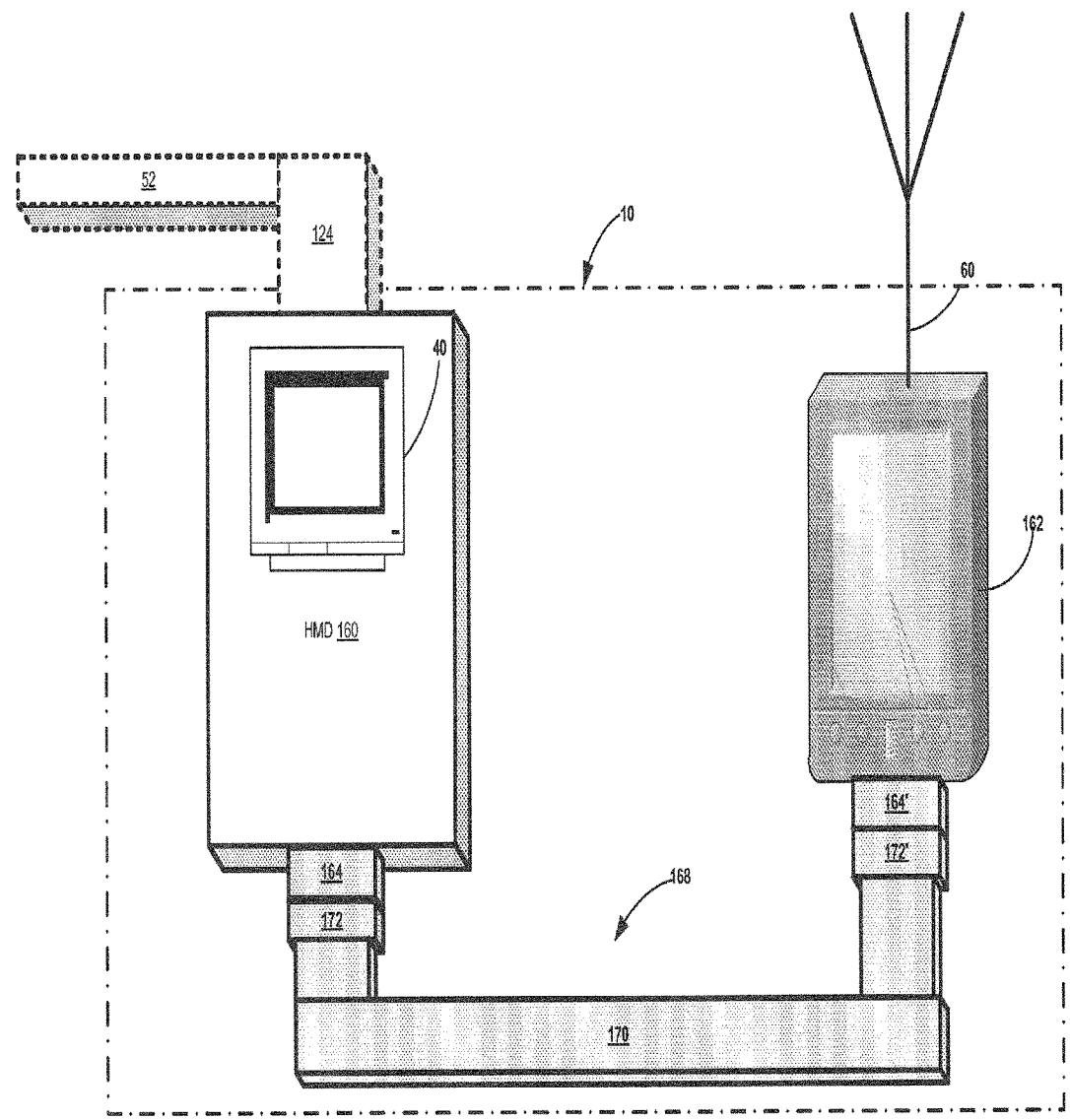
FIG. 7 illustrates an embodiment of a wired connection between a HMD and a WID, also showing an optional adaptor.

Referring to FIG. 7, an embodiment of the connection is shown. In this figure, a hardware (or "wired") connection is shown, i.e., an adaptor 168, disposed between a HMD 160 and a WID 162. The HMD 160 may connect to an exercise machine via a connector 52 with optional adaptor 124. This connection may also be wireless as has been described. In most circumstances, it is assumed that the varieties of HMDs will vary more widely than the varieties of WIDs. Accordingly, HMD 160 will likely have one of a variety of types of connectors for input/output purposes, here shown as a connector 164. Connector 164 mates with a connector 172 of adaptor 168. At another point on adaptor 168 is a connector 172' for connecting to a generic input/output port 164' on WID 162. A cable 170 is disposed between the two connectors, cable 170 capable of including adaptor circuitry if desired.

Of course, the use and structure of adaptor 168, between HMD 160 and WID 162, depends on factors such as the prevalence of an industry standard for such communications. In other words, if the output of HMD 160 is readily acceptable to WID 162, then the same may be directly connected or may be connected via a simple cable, the same basically extending from pin-to-pin. For example, a standard Universal Serial Bus (USB) or serial cable (RS232) may be used if the input/output ports between the HMD and the WID are compatible. Otherwise, a suitable adaptor circuit that provides for appropriate signal and pin conversion may be employed. For example, a standard USB-to-serial (RS232) cable or the like may be used as required. The connection may also be an input for data, e.g. a USB port or phone jack or other such wired input, or a media storage device, again employing an adaptor circuit if required.

Port 164 can be used to communicate with HMD 160 and connector 164 via a number of types of wired connections, including USB, or Firewire. In some cases, optional adaptor 168 may also be employed.

In other embodiments, such as for devices connected to proprietary connectors, a less standard and perhaps proprietary pin-out may be required.

Figure 8:
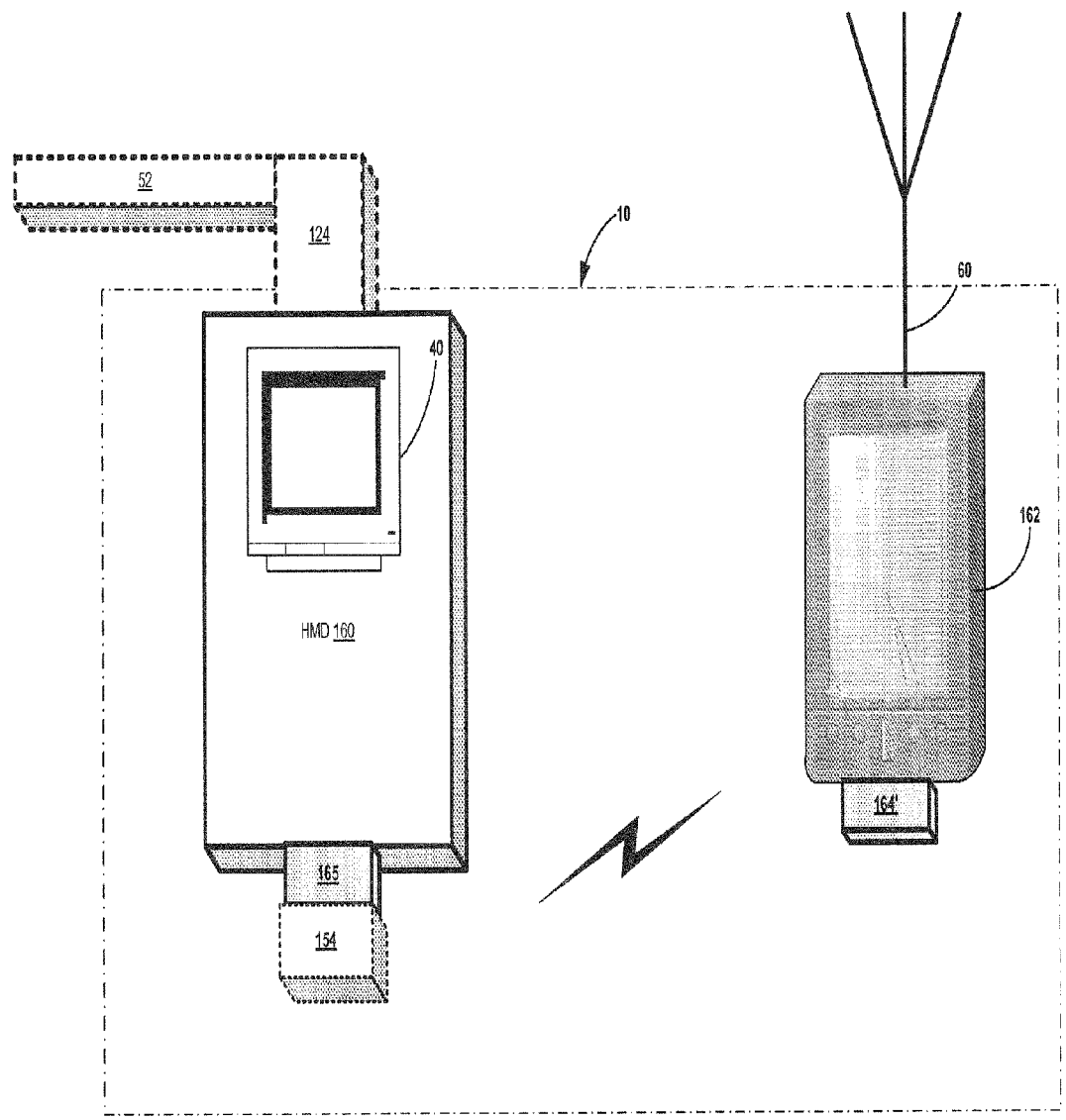
FIG. 8 illustrates an embodiment of a wireless connection between a HMD and a WID, showing a different type of optional adaptor than that in FIG. 9.

Referring to FIG. 8, an embodiment of a wireless implementation of the WEMA 10 is shown. In FIG. 8, a wireless connection is shown between HMD 160 and WID 162. HMD 160 may have an integral wireless modulator/demodulator disposed within (not shown). More likely, however, is that HMD 160 has an adaptor 154 connectable thereto which performs these functions. Adapter 154 may plug into a connector 165 on HMD 160. WID 162 may have an integral wireless modulator/demodulator (not shown), although an adaptor can also be used in this context.

While the device shown in FIG. 8 is described in the context of general wireless communications, various protocols may be employed. For radio frequency communications, a variety of 802.11 protocols, 802.15 protocols, other IEEE 802 family protocols, short-range wireless transmission methods such as Bluetooth®, wireless universal serial bus protocols (W-USB), or other wireless transmission methods may be advantageously employed. Other techniques employing a similar configuration include those employing IR, microwaves, optical techniques including lasers, and so on.

It should be understood that the above is merely exemplary, and that the form of the adaptor may vary widely between HMDs and WIDs.

As noted above, besides the exercise data transmission from HMDs, other sorts of transmissions may also occur. For example, visual data, such as photographs or videos, may be transferred as an indication of the user's performance condition and to aid remote analysis. Alternatively, other visual indications of a user's status, such as graphical or other outputs of HMDs, may provide information useful for a trainer, coach, or other reviewer.

In certain embodiments, a set of visual data from a camera or from an HMD and voice communication may be transmitted via the telecommunications infrastructure from the WID. The visual data may thus be sent via an appropriate protocol to a server for retrieval and analysis by a trainer, coach or other reviewer.

The advent of multimedia mobile phones and other WIDs that include a digital camera (or are equipped with a link to one) allow the capture and transmission of photographic images using low-cost consumer devices. Embodiments of the invention may employ these in combination with HMDs.

It will be understood that the above description of a "Method And Apparatus For Exercise Monitoring Combining Exercise Monitoring and Visual Data With Wireless Internet Connectivity" has been with respect to particular embodiments of the invention. While this description is fully capable of attaining the objects of the invention, it is understood that the same is merely representative of the broad scope of the invention envisioned, and that numerous variations of the above embodiments may be known or may become known or are obvious or may become obvious to one of ordinary skill in the art, and these variations are fully within the broad scope of the invention. For example, while certain wireless technologies have been described herein, other such wireless technologies may also be employed. Furthermore, while various types of exercise monitors have been mentioned, numerous other types may also be used in the embodiments of the invention, including types of devices that are incorporated within the WID. Accordingly, the scope of the invention is to be limited only by the claims appended hereto, and equivalents thereof. In these claims, a reference to an element in the singular is not intended to mean "one and only one" unless explicitly stated. Rather, the same is intended to mean "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present invention is intended to be dedicated to the public regardless of whether the element, component, or method step is explicitly recited in the claims. No claim element herein is to be construed under the provisions of 35 U.S.C. 112, para. 6, unless the element is expressly recited using the phrase "means for".

What is claimed is:

1. A system for monitoring exercise, comprising:
    a mobile internet device configured to be carried on a person, the mobile internet device including:
        a keyboard, keypad, or voice processing technology for receiving user input, an integral digital camera, and a generic port providing a connection to an exercise monitoring device;
        a communications port providing an interactive wireless connection with one or more internet servers;
        a non-transitory computer readable medium having instructions stored thereon for providing a user interface for displaying visual images including graphics, photographs, and video clips;
        the non-transitory computer readable medium further having instructions stored thereon for performing a method comprising steps of:
            receiving a first type of data that is physiological data measured during exercise, and receiving a second type of data that is an amount of exercise work performed;
            receiving a third type of data representing visual images captured by the camera, and
            transmitting the first type of data measuring the physiological data, the second type of data measuring the quantitative amount of exercise work performed, and the third type of data representing the visual images, to one or more internet servers, and
    a non-transitory computer readable medium residing on one or more internet servers having instructions stored thereon defining a server application for performing a method comprising steps of:
        receiving the first type of data that is the physiological data, and receiving the second type of data that is a quantitative amount of exercise work performed, and receiving the third type of data representing visual images from the mobile internet device;
        processing the first, second, and third types of data;
        transmitting the processed data to the mobile internet device in response; and
        transmitting the processed data to a second mobile device, whereby a user of the second mobile device may review the transmitted data and images;
        wherein the non-transitory computer readable medium of the wireless internet device further has instructions for causing the wireless internet device to receive and display the processed data on the user interface of the wireless internet device.

2. The system of claim 1, wherein the mobile internet device is selected from the group comprising: a watch, eyewear, apparel, or other device configured to be worn by a person.

3. The system of claim 1, further comprising a GPS device, an accelerometer, or a timer, integral within the mobile internet device or connected to it, and wherein the data measuring a quantitative amount of exercise work performed is received from the GPS device, the accelerometer, or the timer.

4. The system of claim 1, wherein the first or second types of data, or both, are received from the generic port, and wherein the generic port for connection to an exercise monitoring device is adapted to receive signals from a device selected from the group comprising: a heart rate monitor, a respiration rate monitor, a blood pressure monitor, a temperature monitor, an accelerometer, a pedometer, a GPS device, a timer; a device tracking, rate, intensity, distance, duration, or total amount of exercise; a body weight scale, a body fat gauge, a biofeedback device, a treadmill, a rowing machine, an exercise bicycle, or a stepper.

5. The system of claim 1, wherein the generic port for connection to an exercise monitoring device is configured to provide a wired connection.

6. The system of claim 1, wherein the generic port for connection to an exercise monitoring device is configured to provide a wireless connection, that employs a protocol selected from a variety of 802.11, Bluetooth, or other short range wireless transmission methods.

7. The system of claim 1, wherein the communications port providing an interactive wireless connection to one or more internet servers is configured to provide a wireless link that employs a protocol selected from a variety of 802.11, other IEEE family protocols, cellular, or other RF protocols.

8. A method of monitoring exercise using a mobile internet device wherein the mobile internet device is a device configured to be carried on a person and including a keyboard, keypad, or voice processing technology for user input, a digital camera, and a display for data or images; the mobile internet device connected in wireless communication with a network, comprising:

receiving a first type of data that is physiological data measured during exercise, and further receiving a second type of data, the second type of data being an amount of exercise work performed;

receiving a third type of data representing visual images captured by the digital camera, the visual images including photographic or video images; and displaying the first, second, or third types of data on the mobile internet device;

transmitting the first, second, or third types of data to one or more internet servers; and transmitting from the one or more internet servers the processed data to a second mobile device, whereby a user of the second mobile device may review the transmitted data and images.

9. The method of claim 8, wherein the mobile internet device is selected from the group comprising: a watch, eyewear, apparel, or other device configured to be worn by a person.

10. A system for monitoring exercise, comprising:

a mobile internet device configured to be carried on a person, the mobile internet device including:

a keyboard, keypad, or voice processing technology for receiving user input, an integral digital camera, and a generic port providing a connection to an exercise monitoring device;

a communications port providing an interactive wireless connection with one or more internet servers;

a non-transitory computer readable medium having instructions stored thereon for providing a user interface for displaying visual images including graphics, photographs, and video clips;

the non-transitory computer readable medium further having instructions stored thereon for performing a method comprising steps of:

receiving a first type of data that is physiological data measured during exercise, and receiving a second type of data that is an amount of exercise work performed;

receiving a third type of data representing visual images captured by the camera, and transmitting the first type of data measuring the physiological data, the second type of data measuring the quantitative amount of exercise work performed, and the third type of data representing the visual images, to one or more internet servers, and a non-transitory computer readable medium residing on one or more internet servers having instructions stored thereon defining a server application for performing a method comprising steps of:

receiving the first type of data that is the physiological data, and receiving the second type of data that is a quantitative amount of exercise work performed, and receiving the third type of data representing visual images from the mobile internet device;

processing the first, second, and third types of data;

transmitting the processed data to the mobile internet device in response; and sharing the physiological data related to exercise, or the data measuring a quantitative amount of exercise work performed, or the visual images related to exercise, or combinations thereof, with multiple other mobile internet devices;

wherein the non-transitory computer readable medium of the wireless internet device further has instructions for causing the wireless internet device to receive and display the processed data on the user interface of the wireless internet device.

11. A method of monitoring exercise using a mobile internet device wherein the mobile internet device is a device configured to be carried on a person and including a keyboard, keypad, or voice processing technology for user input, a digital camera, and a display for data or images; the mobile internet device connected in wireless communication with a network, comprising:

receiving a first type of data that is physiological data measured during exercise, and further receiving a second type of data, the second type of data being an amount of exercise work performed;

receiving a third type of data representing visual images captured by the digital camera, the visual images including photographic or video images;

displaying the first, second, or third types of data on the mobile internet device; and sharing the physiological data related to exercise, or the data measuring a quantitative amount of exercise work performed, or the visual images related to exercise, or combinations thereof, with multiple mobile internet devices.

* * * * *